Dec. 27, 1960 KEISO ISHIZU Plant Pat. 2,008
CHRYSANTHEMUM PLANT
Filed March 17, 1960
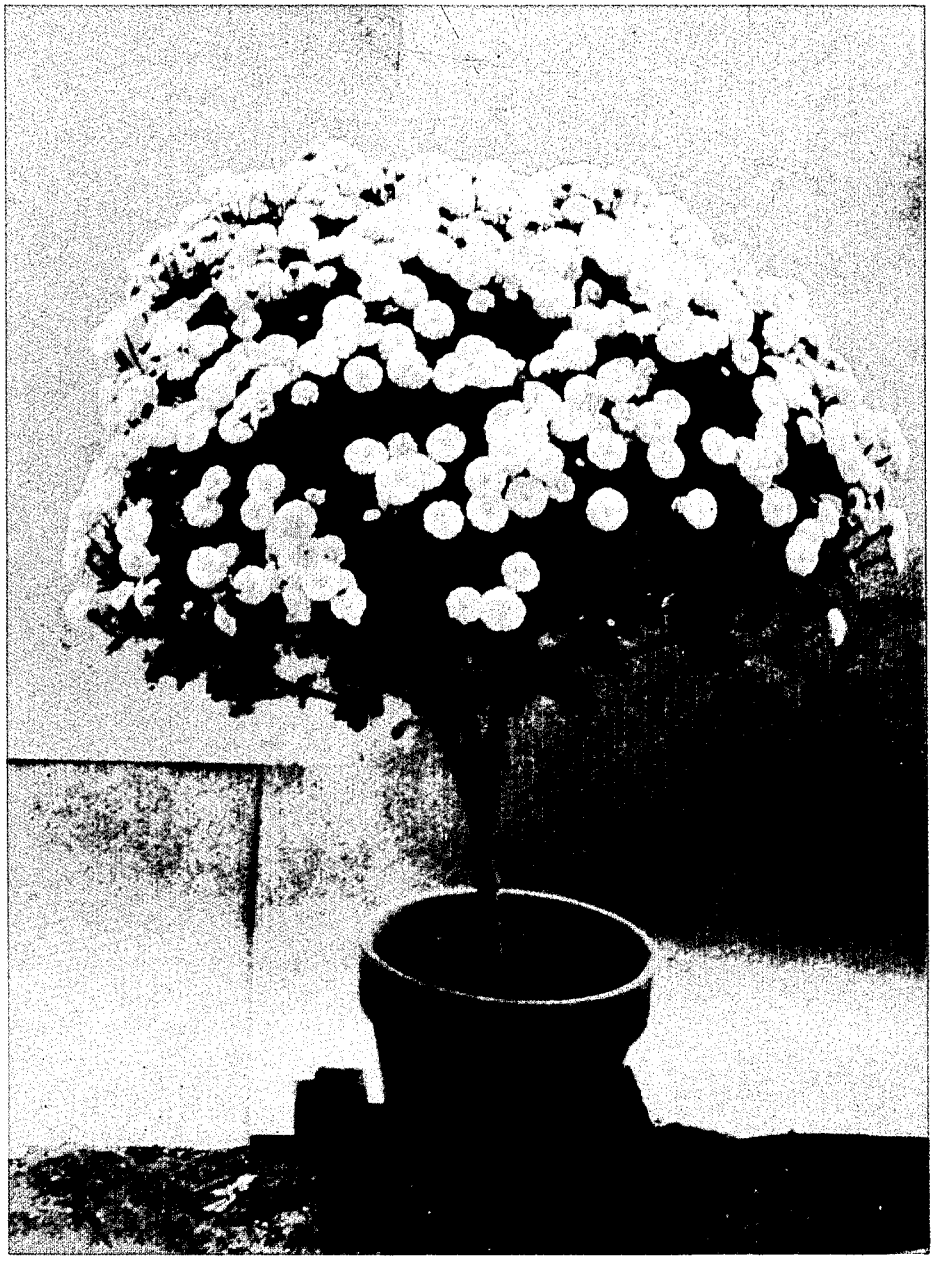
INVENTOR
Keiso Ishizu
BY Robbs & Robb
ATTORNEYS United States Patent Office Plant Pat. 2,008
Patented Dec. 27, 1960

2,008

CHRYSANTHEMUM PLANT

Keiso Ishizu, San Gabriel, Calif.

Filed Mar. 17, 1960, Ser. No. 15,778

1 Claim. (Cl. 47—60)

The present invention relates to a new and distinct variety of chrysanthemum plant of the semi-ball, pompom type, which was originated by me by planting seeds of the variety known as "April Showers" (unpatented), said latter parent variety having been originally acquired by me as a gift, and the origin of which is unknown to me.

The parent variety "April Showers" is particularly characterized by its short, compact and completely self-branching habits of growth, with short stems and peduncles, thus resulting in stocky and bushy plants which stand erect without need of support. This variety bears an abundance of flowers of deep lavender pink color, but the plants have an important shortcoming as the result of being susceptible to "blindness" when planted late in the season (usually after July first).

I accordingly attempted to create an improved chrysanthemum variety of the general type and habits of "April Showers," as well as a change in the flower color, and in approaching these objectives, I harvested seeds from plants of "April Showers" and planted said seeds on my cultivated property at San Gabriel, California. While chrysanthemums are heterozygote, and frequently do not reveal the identity of their parents nor carry forward desirable characteristics of their parents until "back crosses" are made, one of the seedlings which I derived from the plantings referred to above successfully achieved the objectives which I was seeking, as evidenced by the following unique combination of characteristics which are outstanding in my new variety and which distinguish it from its parent, as well as from all other varieties of which I am aware:

(1) Extremely bushy and self-branching habits of growth, with stocky trunk growth that requires no extraneous supports, thus making the plants ideally suited to shaping into tree or "Bonsai" forms;

(2) A rapid growing habit (much more rapid than "April Showers"), which results in plants of larger size than plants of "April Showers";

(3) Absence of "blindness" even in late plantings; and (4) An iridescent Aureolin Yellow general color tonality of the flowers.

My new chrysanthemum variety has proved itself to be suitable for creating general garden effects, and particularly for border plantings, as well as for use of cut flowers in bouquets. In addition to its suitability for shaping into tree form, it is also suitable for dish plantings.

Asexual reproduction of the new variety by both tip cuttings and stolons as performed by me at San Gabriel, California, shows that the foregoing characteristics and distinctions come true to form and are established and transmitted through succeeding propagations.

The accompanying drawing shows a typical blooming plant of my new variety as shaped into tree form and as depicted in color as nearly true as it is reasonably possible to make the same in a color illustration of this character.

The following is a detailed description of the new variety, with color terminology in accordance with the Horticultural Color Chart of the British Color Council, as based upon specimens grown by me at San Gabriel, California:

Parentage: Seedling of "April Showers."
Classification: Semi-ball, pompom type.
Growth: Very stocky; extremely self-branching.
Cold resistance: Winter-hardy in southern California.
Blooming period: In the southern California climatic area, the plants attain full bloom about October 25, and the blooms last about a month or more.

*Flower*

Bud:
- *Color.*—When sepals first divide—Lemon Yellow, Plate 4/1. When petals begin to unfurl—Empire Yellow, Plate 603. When half-blown: inside of petals—Aureolin Yellow, Plate 3; reverse of petals—Empire Yellow, Plate 603.
- *Peduncle.* — Strength — sturdy. Color — Lavender Green, Plate ooo761/1.

Bloom:
- *Size.*—Average about 1 inch in diameter.
- *Stem.*—Stiff.
- *Form.*—Semi-globular.
- *Petalage.*—Extremely fully double.
- *Color.*—Center of flower—Aureolin Yellow, Plate 3. Outer petals—Aureolin Yellow, Plate 3. Base of petals—Pod Green, Plate o61. Inside of petals—Aureolin Yellow, Plate 3. Reverse of petals—Empire Yellow, Plate 603. General tonality—Aureolin Yellow, Plate 3.
- *Petals.*—Texture—firm. Form—oval.
- *Fragrance.*—Characteristically chrysanthemum.

*Plant*

Form: Stocky; upright; very bushy.
Growth: Vigorous.
Foliage:
- *Size.*—Medium.
- *Quantity.*—Normal.
- *Color.*—Upper side—Spinach Green, Plate o960/2. Reverse side—Sage Green, Plate ooo861/1.
- *Texture.*—Medium thickness; glossy.

I claim:

A new and distinct variety of chrysanthemum plant of the semi-ball, pompom type, substantially as herein shown and described, characterized particularly as to novelty by the unique combination of extremely bushy and self-branching habits of growth, with stocky trunk growth that requires no extraneous support and being suitable for shaping into tree or "Bonsai" forms, as well as for cut flower bouquets and general garden effects, including border plantings, a rapid growing habit, with consequent attainment of large plant size, the absence of "blindness" even in late plantings, and an iridescent Aureolin Yellow general color tonality of the flowers.

No references cited.